US011234685B2

United States Patent
Xu et al.

(10) Patent No.: US 11,234,685 B2
(45) Date of Patent: Feb. 1, 2022

(54) FLEXIBLE SURGICAL INSTRUMENT SYSTEM

(71) Applicant: BEIJING SURGERII TECHNOLOGY CO., LTD., Beijing (CN)

(72) Inventors: Kai Xu, Beijing (CN); Tianlai Dong, Beijing (CN); Zhengchen Dai, Beijing (CN); Jiangran Zhao, Beijing (CN); Huichao Zhang, Beijing (CN); Shu'an Zhang, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 392 days.

(21) Appl. No.: 16/329,747

(22) PCT Filed: Aug. 31, 2017

(86) PCT No.: PCT/CN2017/099886
§ 371 (c)(1),
(2) Date: Feb. 28, 2019

(87) PCT Pub. No.: WO2018/041213
PCT Pub. Date: Mar. 8, 2018

(65) Prior Publication Data
US 2019/0192129 A1     Jun. 27, 2019

(30) Foreign Application Priority Data
Aug. 31, 2016 (CN) .......................... 201610797565.6

(51) Int. Cl.
*A61B 17/00*     (2006.01)
*A61B 34/00*     (2016.01)
(Continued)

(52) U.S. Cl.
CPC ........ *A61B 17/00234* (2013.01); *A61B 34/30* (2016.02); *A61B 34/71* (2016.02);
(Continued)

(58) Field of Classification Search
CPC .... A61B 17/00234; A61B 2017/00305; A61B 2017/00318; A61B 2034/301;
(Continued)

(56) References Cited

U.S. PATENT DOCUMENTS

| | | |
|---|---|---|
| 2013/0090763 A1 | 4/2013 | Simaan et al. |
| 2014/0005661 A1 | 1/2014 | Shelton, IV et al. |

(Continued)

FOREIGN PATENT DOCUMENTS

| | | |
|---|---|---|
| CN | 103085083 A | 5/2013 |
| CN | 103315781 A | 9/2013 |

(Continued)

OTHER PUBLICATIONS

State Intellectual Property Office of People's Republic of China, Office Action and Search Report Issued in Application No. 201610796082.4, dated Jun. 21, 2018.
(Continued)

*Primary Examiner* — Mohamed G Gabr
(74) *Attorney, Agent, or Firm* — McCoy Russell LLP

(57) ABSTRACT

Disclosed is a flexible surgical instrument system (100), comprising a flexible surgical instrument (10) composed of a distal structural body (11), a proximal structural body (12), a driving transmission mechanism (13) and a middle connecting body (14), wherein a surgical end effector (111) is located at a distal end of the distal structural body (11), a proximal end of the distal structural body (11) is linked to the middle connecting body (14), and the driving transmission mechanism (13) is linked to the proximal structural body (12) via the middle connecting body (14); the distal
(Continued)

structural body (11) comprises at least one distal structural segment (112, 113), wherein each distal structural segment (112, 113) comprises a distal fixing disk (115, 118) and structural backbones (116, 119); the proximal structural body (12) comprises at least one proximal structural segment (120, 121), wherein each proximal structural segment (120, 121) comprises a proximal fixing disk (122, 126), structural backbones (124, 128), and driving backbones (125, 129); and the driving transmission mechanism (13) comprises an introducing part, a driving part, and a reversing part.

19 Claims, 13 Drawing Sheets

(51) Int. Cl.
    *A61B 34/30*     (2016.01)
    *A61M 25/01*     (2006.01)
    *A61M 25/00*     (2006.01)
    *A61B 46/10*     (2016.01)

(52) U.S. Cl.
    CPC ..... *A61B 46/10* (2016.02); *A61B 2017/00305* (2013.01); *A61B 2017/00318* (2013.01); *A61B 2034/301* (2016.02); *A61B 2034/305* (2016.02); *A61M 25/0043* (2013.01); *A61M 25/0144* (2013.01)

(58) Field of Classification Search
    CPC ........ A61B 2034/305; A61B 2034/306; A61B 34/30; A61B 34/70; A61B 34/71; A61B 46/10; A61M 25/0043; A61M 25/0144
See application file for complete search history.

(56) References Cited

U.S. PATENT DOCUMENTS

| | | | |
|---|---|---|---|
| 2014/0330432 A1 | 11/2014 | Simaan et al. | |
| 2015/0313619 A1 | 11/2015 | Tadano et al. | |
| 2015/0352728 A1* | 12/2015 | Wang | A61B 1/00 74/490.04 |

FOREIGN PATENT DOCUMENTS

| | | | |
|---|---|---|---|
| CN | 103340707 | A | 10/2013 |
| CN | 103707322 | A | 4/2014 |
| CN | 103948435 | A | 7/2014 |
| CN | 104758060 | A | 7/2015 |
| CN | 103707322 | B | 4/2016 |
| CN | 106175850 | A | 12/2016 |
| EP | 2594211 | A1 | 5/2013 |
| WO | 2008045333 | A2 | 4/2008 |
| WO | 2015023813 | A1 | 2/2015 |
| WO | 2016030457 | A1 | 3/2016 |

OTHER PUBLICATIONS

European Patent Office, Supplementary European Search Report Issued in Application No. 17845515.0, dated May 29, 2020, Germany, 3 pages.

ISA State Intellectual Property Office of the People's Republic of China, International Search Report Issued in Application No. PCT/CN2017/099886, dated Oct. 26, 2017, WIPO, 4 pages.

* cited by examiner

FLEXIBLE SURGICAL INSTRUMENT SYSTEM

CROSS REFERENCE TO RELATED APPLICATIONS

The present patent application is a U.S. National Phase of Chinese International Application No. PCT/CN2017/099886 entitled "FLEXIBLE SURGICAL INSTRUMENT SYSTEM" and filed on Aug. 31, 2017. Chinese International Application No. PCT/CN2017/099886 claims priority to Chinese Patent Application No. 201610797565.6 filed on Aug. 31, 2016. The entire contents of each of the above-identified applications are incorporated herein by reference for all purposes.

TECHNICAL FIELD

The present application relates to a flexible surgical instrument system.

BACKGROUND ART

Multi-port laparoscopic minimally invasive surgery has occupied an important position in surgery because of it having small incision and rapid postoperative recovery. At present, the da Vinci surgical robot of the Intuitive Surgical, Inc. can assist doctors in completing the multi-port laparoscopic minimally invasive surgery.

After the multi-port laparoscopic surgery, single-port laparoscopic surgery and natural orifice transluminal non-invasive surgery have also been further developed and have less trauma to the patient and higher postoperative outcomes.

SUMMARY OF THE INVENTION

In view of this, the present application discloses a flexible surgical instrument system, which can be better applied to a single-port laparoscopic surgery robotic system through a single surgical incision, and can also be applied to a multi-port laparoscopic surgery robotic system.

In order to achieve the above object, the present application provides the following technical solutions. According to a first aspect of the present application, provided is a flexible surgical instrument system, comprising a flexible surgical instrument composed of a distal structural body, a proximal structural body, a driving transmission mechanism and a middle connecting body, wherein a proximal end of the distal structural body is linked to the middle connecting body, and the driving transmission mechanism is linked to the proximal structural body via the middle connecting body; the distal structural body comprises at least one distal structural segment each comprising a distal fixing disk and structural backbones; the proximal structural body comprises at least one proximal structural segment each comprising a proximal fixing disk, structural backbones, and driving backbones; and the driving transmission mechanism comprises an introducing part, a driving part, and a reversing part, wherein the introducing part is configured to introduce a rotational power from the outside into the driving part, the reversing part is configured to implement a cooperative motion of the driving part, and the driving part is configured to convert the rotational power into a linear power to cooperatively push/pull the driving backbones to turn the proximal structural segment in any direction, and in turn to drive the distal structural segment to turn in an opposite direction.

In an embodiment, the middle connecting body comprises a proximal structural body fixing end disk, structural backbone guide channels, and driving backbone guide channels, wherein a distal end of the structural backbone guide channel is fixedly connected to the driving transmission mechanism, and a proximal end thereof is fixedly connected to the proximal structural body fixing end disk; distal and proximal ends of the driving backbone guide channel are fixedly connected to the driving transmission mechanism and the proximal structural body fixing end disk, respectively; when the structural backbones on the distal structural segment are securely connected, in one-to-one correspondence, to or are the same as the structural backbones on the proximal structural segment, a proximal end of the structural backbone is securely connected to the proximal fixing disk, and a distal end thereof passes through the structural backbone guide channel and is then securely connected to the distal fixing disk; and a distal end of the driving backbone is fixedly connected to the driving part, and a proximal end thereof passes through the driving backbone guide channel and is then fixedly connected to the proximal fixing disk.

In an embodiment, the driving transmission mechanism further comprises a main body part, and the driving part comprises several linear driving mechanisms, wherein each of the linear driving mechanisms comprises a first threaded rod rotatably mounted on the main body part, and a first slider threadedly fitted with the first threaded rod; a proximal end of the first threaded rod is securely connected to the introducing part, and a distal end thereof extends into the reversing part; and the first slider of each of the linear driving mechanisms, functioning as an output end, is securely connected, in one-to-one correspondence, to the driving backbones.

In an embodiment, the introducing part comprises a driving shaft rotatably mounted on the main body part, a first male coupling securely connected to a proximal end of the driving shaft, and a coupling securely connected to a distal end of the driving shaft. The reversing part comprises several sets of reversing gears mounted on the main body part, wherein each set of reversing gears comprises two intermeshing gears securely connected to two of the first threaded rods, respectively. The rotational power from the outside is transmitted to the first threaded rod located inside the driving part through the first male coupling, the driving shaft and the coupling, and drives the corresponding two first threaded rods to rotate in opposite directions by means of the set of reversing gears, and the first threaded rods drive the first sliders to slide in opposite directions, thereby converting the rotational power into a linear power for cooperatively pushing or pulling the driving backbones to turn the proximal structural segment in any direction, and in turn to drive the distal structural segment to turn in an opposite direction.

In an embodiment, the main body part comprises a distal cover plate, a distal fixing plate, a middle fixing plate, and a proximal fixing plate, which are securely connected to form an integral body. The driving shaft is rotatably mounted between the proximal fixing plate and the middle fixing plate. The first threaded rod is rotatably mounted between the distal fixing plate and the middle fixing plate. The set of reversing gears are mounted between the distal cover plate and the distal fixing plate.

In an embodiment, the flexible surgical instrument system further comprises a surgical end effector located at a distal end of the distal structural body. The driving transmission mechanism further comprises a surgical end effector driving mechanism, wherein the surgical end effector driving mechanism comprises a second threaded rod rotatably mounted on the main body part, a second slider threadedly fitted with the second threaded rod, and a surgical end effector actuation wire with a proximal end thereof being securely connected to the second slider, and a distal end thereof passing through the distal structural body and then being securely connected to the surgical end effector. A proximal end of the second threaded rod is securely connected to the coupling, the rotational power from the outside is transmitted to the second threaded rod through the first male coupling, the driving shaft and the coupling, and the second threaded rod drives the second slider to linearly slide, and in turn pushes/pulls the surgical end effector actuation wire to control the action of the surgical end effector.

In an embodiment, the surgical actuator driving mechanism further comprises a fixing end plate fixed onto the middle fixing plate via several support columns, and a actuation wire guide channel with a proximal end being fixed onto the fixing end plate, and a distal end extending into the first distal structural segment and being fixed onto a distal spacer disk of the first distal structural segment. The second threaded rod is rotatably mounted between the fixing end disk and the middle fixing plate. A proximal end of the surgical end effector actuation wire is securely connected to the second slider, and a distal end thereof passes through the fixing end plate, the actuation wire guide channel and the distal structural body and is then securely connected to the surgical end effector.

In an embodiment, the linear driving mechanism further comprises a shaft fixedly connected between the distal fixing plate and the middle fixing plate, the first slider being slidably connected to the shaft. The second slider is slidably connected to one of the support columns.

In an embodiment, the system further comprises a driving unit linked to the driving transmission mechanism, the driving unit comprising a driving motor, an input gear connected to an output shaft of the driving motor, an idle gear and an output gear meshing with the input gear, a second male coupling fixedly connected to the output gear, and female couplings respectively connected to the first male coupling and the second male coupling. The driving motor transmits the rotational motion to the second male coupling through the input gear, the idle gear and the output gear, and drives the driving shaft to rotate via the female couplings and the first male coupling.

In an embodiment, the driving unit further comprises a connection plate arranged at a proximal end of the driving unit, and the flexible surgical instrument system is fixedly mounted on an end disk of a multi-degree-of-freedom robotic arm via the connection plate. The multi-degree-of-freedom robotic arm comprises four or more joints, the joints being able to implement the overall lateral deflection and the overall feed freedom of the flexible surgical instrument system with an abdomen entrance point as the fixed point, and being able to implement the overall rotation freedom of the flexible surgical instrument about its own axis.

In an embodiment, the system further comprises a flexible surgical instrument housing forming a housing structure of the flexible surgical instrument with the distal cover plate, and a sterile barrier arranged between the flexible surgical instrument and the driving unit, wherein the proximal structural body, the driving transmission mechanism and the middle connecting body are all located inside the flexible surgical instrument housing. The sterile barrier comprises a structural fixing cylinder connected to the flexible surgical instrument and the driving unit respectively, a sterile barrier cover plate and a sterile barrier base plate fixedly connected to a proximal end of the structural fixing cylinder to form a closed structure, and a sterile membrane fixedly connected to an outer edge of the structural fixing cylinder and coated outside the driving unit and the multi-degree-of-freedom robotic arm. The female couplings are rotatably arranged between the sterile barrier cover plate and the sterile barrier base plate.

In an embodiment, the distal structural segment further comprises a plurality of distal spacer disks distributed therein at intervals, wherein structural backbones of the distal structural segment pass through structural backbone passage holes distributed in each of the distal spacer disks, and have the distal ends thereof fixed onto the distal fixing disk. The proximal structural segment further comprises a plurality of proximal spacer disks distributed therein, wherein the proximal ends of the structural backbones of the proximal structural segment are fixed on the proximal fixing disk and the distal ends thereof pass through the structural backbone passage holes distributed in the proximal spacer disks in sequence, and are then securely connected in one-to-one correspondence to or are the same as the structural backbones of the distal structural segment.

In an embodiment, the structural backbones of the distal structural segment and/or the structural backbones of the proximal structural segment are elastic elongated rods or elongated tubes made of a nickel titanium alloy or stainless steel. In the case of using a plurality of the distal structural segments or a plurality of the proximal structural segments, if the structural backbones of a preceding distal structural segment or proximal structural segment use elastic elongated tubes, the structural backbones of the next distal structural segment or proximal structural segment are able to pass through the elastic elongated tubes or directly pass through the structural backbone passage holes in the distal spacer disks or in the proximal spacer disks. The number of the structural backbones of each of the distal structural segments or the proximal structural segments is three or more.

In an embodiment, the distal structural body is externally covered with an envelope, wherein a proximal end of the envelope is securely connected to the middle fixing plate via a first fixing clamp. The envelope is of a rigid envelope between the distal fixing plate and the middle fixing plate, and of a flexible envelope between the distal fixing plate and the surgical end effector.

In an embodiment, the envelope is further externally covered with an outer sleeve, wherein the outer sleeve is fixed onto the distal fixing plate via a second fixing clamp; if the outer sleeve is a rigid pre-bent sleeve, the outer sleeve passes through a sheath fixed to a single surgical incision, the sheath provides a channel for an instrument required for single-port laparoscopic surgery; and if the outer sleeve is a rigid straight sleeve, the outer sleeve passes through a sheath containing only one channel, the sheath is fixed to a surgical incision.

In an embodiment, the number of proximal structural segments in the proximal structural body is equal to the number of distal structural segments in the distal structural body.

According to a second aspect of the present application, provided is a flexible surgical instrument, comprising a flexible surgical instrument composed of a distal structural body, a proximal structural body, a driving transmission mechanism and a middle connecting body, wherein a proximal end of the distal structural body is linked to the middle connecting body, and the driving transmission mechanism is linked to the proximal structural body via the middle connecting body; the distal structural body comprises at least one distal structural segment each comprising a distal fixing disk and structural backbones; the proximal structural body comprises at least one proximal structural segment each comprising a proximal fixing disk, structural backbones, and driving backbones; and the driving transmission mechanism comprises an introducing part, a driving part, and a reversing part, wherein the introducing part is configured to introduce a rotational power from the outside into the driving part, the reversing part is configured to implement a cooperative motion of the driving part, and the driving part is configured to convert the rotational power into a linear power to cooperatively push or pull the driving backbones to turn the proximal structural segment in any direction, and in turn to drive the distal structural segment to turn in the opposite direction.

The present application adopts the above technical solutions, which have the following advantages: 1. a flexible continuous body structure comprising a proximal structural body, a middle connecting body and a distal structural body is used as the main body and cooperates with a driving transmission mechanism, wherein the distal structural body is linked to the proximal structural body via the middle connecting body, the driving transmission mechanism is linked to the proximal structural body via the middle connecting body, and when the driving transmission mechanism drives the proximal structural segment of the proximal structural body to turn in any direction, the corresponding distal structural segment of the distal structural body correspondingly turns in the opposite direction, and a flexible surgical arm formed by the distal structural body and an envelope is thus capable of turning in any direction; 2. a redundant arrangement of structural backbones (the number thereof being more than three) is used in the distal structural body, the middle connecting body and the proximal structural body, thereby improving the safety, reliability and load capacity of the flexible surgical instrument; 3. the flexible surgical instrument system of the present application can be connected to a multi-degree-of-freedom robotic arm, so that a large-scale motion is realized by the multi-degree-of-freedom robotic arm, and the small-scale precise and flexible motion is realized by the flexible surgical arm in the patient; 4. the surgical end effector actuation wire of the present application enters the interior of the driving transmission mechanism through the distal structural body, and a surgical end effector driving mechanism for driving the surgical end effector actuation wire to perform linear motion is provided inside the driving transmission mechanism, so that the action of the surgical end effector can be controlled; 5. the flexible surgical instrument of the present application is quickly connected to the driving unit via a sterile barrier, thereby effectively isolating the sterilized flexible surgical instrument from other unsterilized parts, and ensuring the clinical practicability of surgery; and 6. if the outer sleeve is a rigid pre-bent sleeve, the present invention can be applied to single-port laparoscopic surgery; and if the outer sleeve is a rigid straight sleeve, the present invention can also be applied to multi-port laparoscopic surgery.

DETAILED DESCRIPTION OF EMBODIMENTS

The embodiments of the present invention will be described below in detail with reference to the accompanying drawings so that the objects, features and advantages of the present invention can be more clearly understood. It should be understood that the embodiments shown in the accompanying drawings are not intended to limit the scope of the present invention, but are intended only to illustrate the essential spirit of the technical solutions of the present invention.

In the single-port laparoscopic surgery and the natural orifice transluminal non-invasive surgery, all surgical instruments including a visual illumination module and a surgical manipulator can have access to the surgical site through a single channel, which is extremely stringent for the preparation of the surgical instruments. In an embodiment, a distal structure of a surgical instrument may consist of multiple rods hinged in series, and is driven by a pulling force from a steel wire rope, so that the surgical instrument can be turned at an articulated joint. Since the steel wire rope has to be continuously tensioned by a pulley, this driving method can hardly lead to further miniaturization of the surgical instrument, and also further improvement of the moving performance of the instrument.

The Intuitive Surgical, Inc. has introduced a da Vinci Single-Site (SS-type da Vinci) surgical robot, in which the original rigid surgical instrument is modified into a semi-rigid surgical instrument and a pre-bent sleeve is additionally provided, which can improve the moving performance of the surgical instrument to a certain extent.

Figure 1:
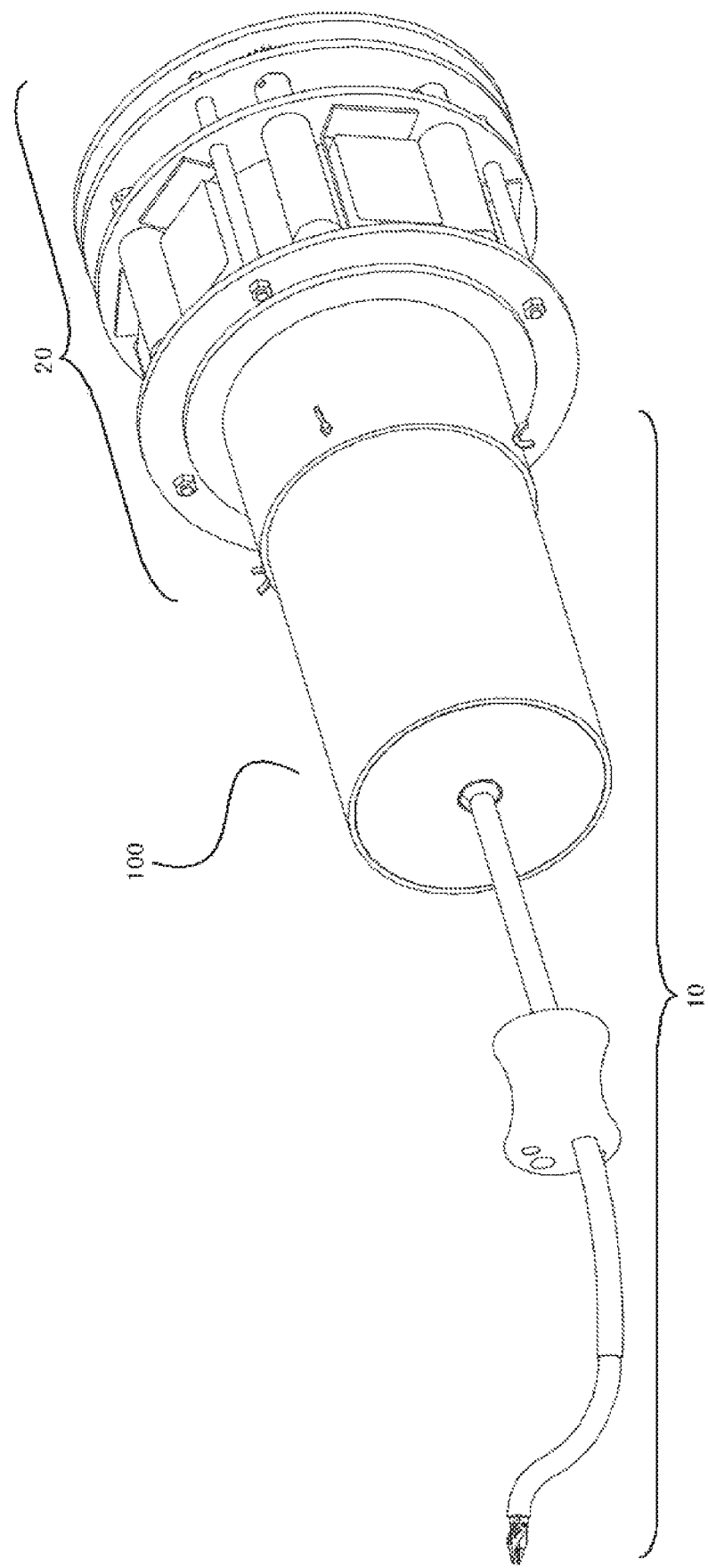
FIG. 1 is an overall structural schematic diagram of a flexible surgical instrument shown in accordance with an example of the present application.

FIG. 1 is an overall structural schematic diagram of a flexible surgical instrument system 100 shown by an example of the present application, which flexible surgical instrument system 100 may comprise a flexible surgical instrument 10 and a driving unit 20.

Figure 2:
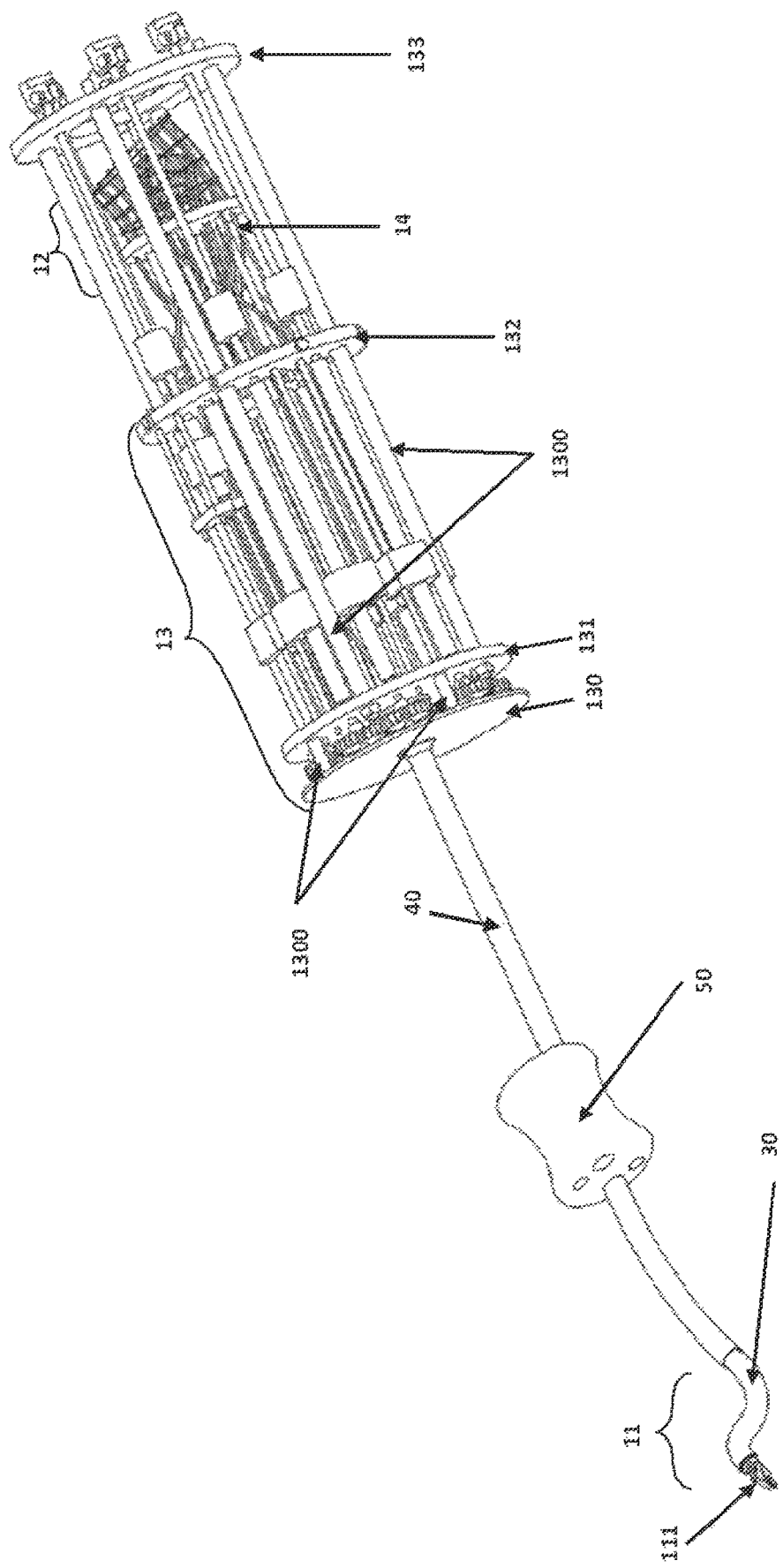
FIG. 2 is a structural schematic diagram of a flexible surgical instrument shown in accordance with an example of the present application.

As shown in FIG. 2, the flexible surgical instrument 10 may comprise a surgical end effector 111, a distal structural body 11, a proximal structural body 12, a driving transmission mechanism 13, and a middle connecting body 14. A proximal end of the distal structural body 11 is linked to the middle connecting body 14, the driving transmission mechanism 13 is linked to the proximal structural body 12 via the middle connecting body 14, and the driving transmission mechanism 13 is linked to the driving unit 20 (not shown in FIG. 2). When the driving unit 20 drives the proximal structural body 12 to bend in any direction by means of the driving transmission mechanism 13, the proximal structural body 12 can transmit a driving force through the middle connecting body 14 to the distal structural body 11, and the distal structural body 11 can correspondingly turn in an opposite direction. The surgical end effector 111 is located at a distal end of a second distal structural segment 113. It should be explained that in the present application, for a certain component, the distal end refers to the end of the component that is away from a surgical operator but close to a surgical site; and the proximal end refers to the end of the component that is close to the operator but away from the surgical site.

Figure 3:
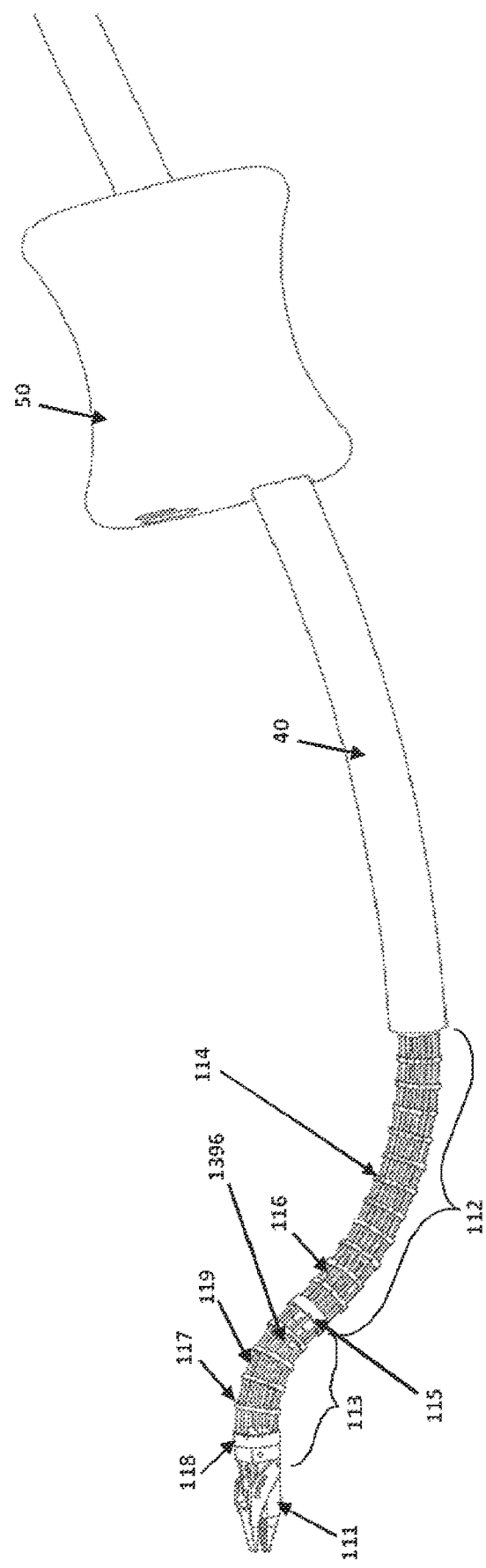
FIG. 3 is a partial structural schematic diagram of a flexible surgical instrument shown in accordance with an example of the present application.
Figure 4:
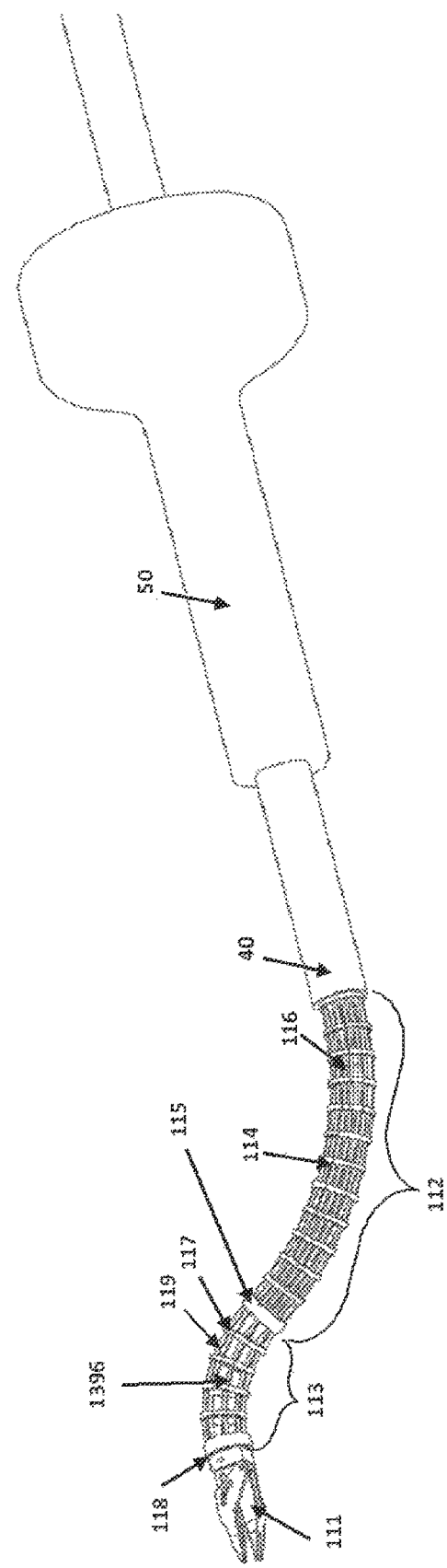
FIG. 4 is a partial structural schematic diagram of a flexible surgical instrument shown in accordance with a further example of the present application.

As shown in FIGS. 3 and 4, the distal structural body 11 may comprise a first distal structural segment 112 and a second distal structural segment 113. The first distal structural segment 112 may comprise first distal spacer disks 114, a first distal fixing disk 115 and first segment structural backbones 116. Several first distal spacer disks 114 may be distributed in the first distal structural segment 112 at intervals, to prevent the first segment structural backbones 116 from being destabilized when being pushed/pulled. A plurality of first segment structural backbones 116 (eight in this embodiment, but not limited thereto) pass through structural backbone passage holes distributed in each first distal spacer disk 114, and the distal ends of the first segment structural backbones 116 may be fixed onto the first distal fixing disk 115.

Similarly, the second distal structural segment 113 may comprise second distal spacer disks 117, a second distal fixing disk 118 and second segment structural backbones 119. Several second distal spacer disks 117 may be distributed in the second distal structural segment 113 at intervals, to prevent the second segment structural backbones 119 from being destabilized when being pushed/pulled. A plurality of the second segment structural backbones 119 pass through structural backbone passage holes distributed in each second distal spacer disk 117, and the distal ends of the second segment structural backbones 119 may be fixed on the second distal fixing disk 118.

It should be noted that the number of the first segment structural backbones 116 and the second segment structural backbones 119 may be three or more, so that the first distal structural segment 112 and the second distal structural segment 113 can turn in any direction.

Figure 5:
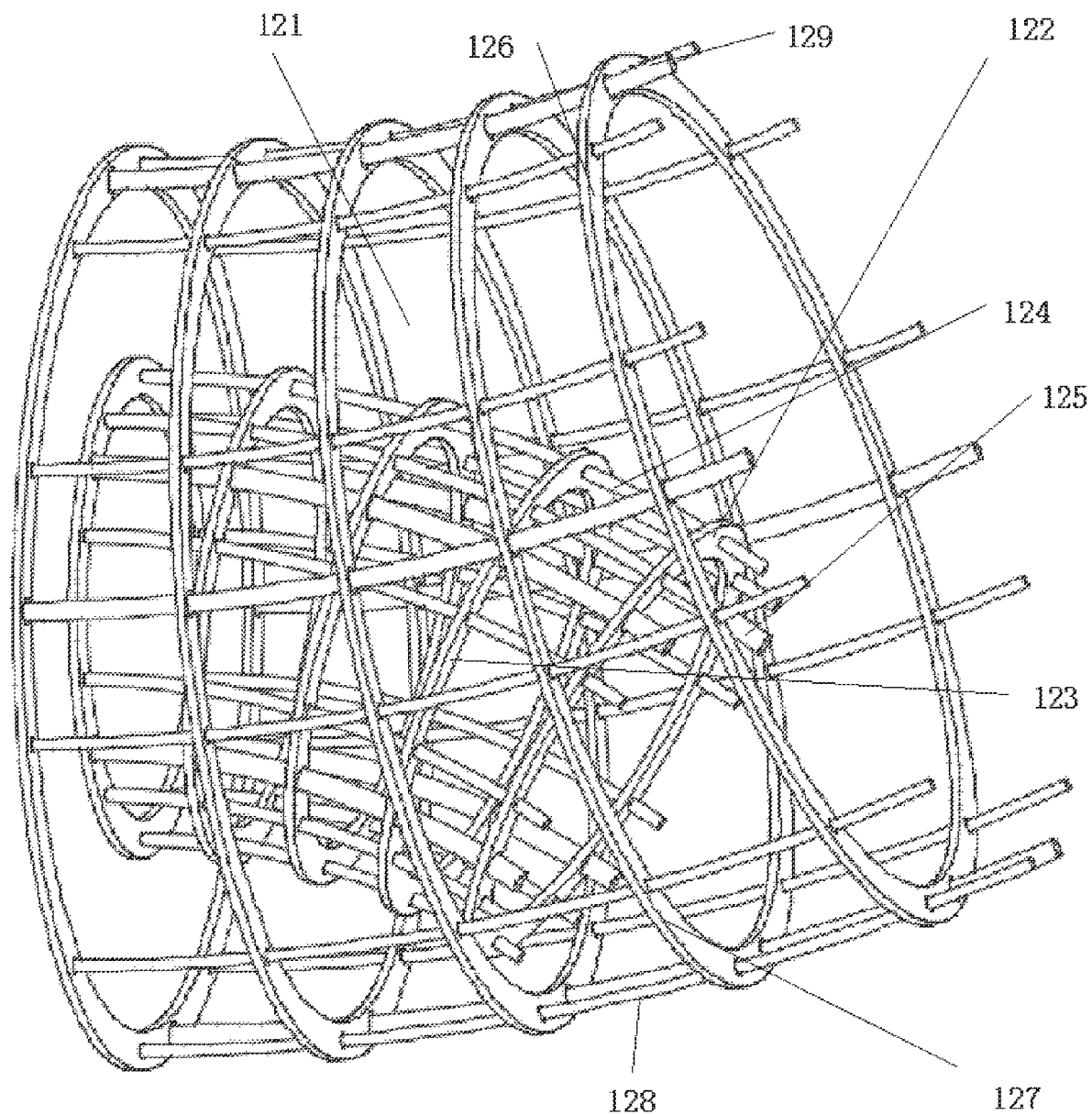
FIG. 5 is a structural schematic diagram of a proximal structural body shown in accordance with an example of the present application.

As shown in FIG. 5, the proximal structural body 12 may comprise a first proximal structural segment 120 and a second proximal structural segment 121, wherein the first proximal structural segment 120 and the second proximal structural segment 121 may be nested inside each other. As shown in FIG. 5, in an embodiment, the first proximal structural segment 120 may be nested inside the second proximal structural segment 121. The first proximal structural segment 120 may comprise a first proximal fixing disk 122, first proximal spacer disks 123, first segment structural backbones 124, and first segment driving backbones 125, and the number of the first segment structural backbones 124 always equals to the number of the first segment structural backbones 116. Several first proximal spacer disks 123 are distributed in the first proximal structural segment 120 at intervals, to prevent the first segment structural backbones 124 and the first segment driving backbones 125 from being destabilized when being pushed or pulled. The first segment structural backbones 124 of the first proximal structural segment 120 are securely connected in one-to-one correspondence to or are the same as the first segment structural backbones 116 of the first distal structural segment 112. The proximal end of each of the first segment structural backbones 124(116) may be fixed onto the first proximal fixing disk 122, and the distal end thereof may pass through the respective one of the structural backbone passage holes distributed in each first proximal spacer disk 123, is guided by the middle connecting body 14 to extend into the first distal structural segment 112, passes through the respective one of the structural backbone passage holes distributed in the first distal spacer disk 114, and is then fixed onto the first distal fixing disk 115. The proximal end of each of the first segment driving backbones 125 (four in this embodiment, but not limited thereto) may be fixed onto the first proximal fixing disk 122, and the distal ends thereof are all fixed in the driving transmission mechanism 13.

Similarly, the second proximal structural segment 121 may comprise a second proximal fixing disk 126, second proximal spacer disks 127, second segment structural backbones 128, and second segment driving backbones 129, and the number of the second segment structural backbones 128 always equals to the number of the second segment structural backbones 119. The second segment structural backbones 128 of the second proximal structural segment 121 may be securely connected in one-to-one correspondence to or be the same as the second segment structural backbones 119 of the second distal structural segment 113. Several second proximal spacer disks 127 may be distributed in the second proximal structural segment 121 at intervals, to prevent the second segment structural backbones 128 and the second segment driving backbones 129 from being destabilized when being pushed or pulled. The proximal end of each of the second segment structural backbones 128 (119) may be fixed onto the second proximal fixing disk 126, and the distal end thereof may pass through the respective one of the structural backbone passage holes distributed in each second proximal spacer disk 127, is guided by the middle connecting body 14, passes through the first distal structural segment 112 to extend into the second distal structural segment 113, passes through the respective one of the structural backbone passage holes distributed in the second distal spacer disk 117, and is then fixed onto the second distal fixing disk 118. The proximal end of each of the second segment driving backbones 129 (four in this embodiment, but not limited thereto) may be fixed onto the second proximal fixing disk 126, and the distal ends thereof are all fixed in the driving transmission mechanism 13.

It should be noted that the number of the first segment driving backbones 125 and the second segment driving backbones 129 may respectively be three or more, so that the first proximal structural segment 120 and the second proximal structural segment 121 can turn in any direction.

In an embodiment, the structural backbones in the above distal structural body 11 and/or the structural backbones and driving backbones in the proximal structural body 12 may be elastic elongated rods or elongated tubes, and the material thereof may be nickel titanium alloy, stainless steel, etc. In the case of using the plurality of distal structural segments or proximal structural segments, if the structural backbones of a preceding distal structural segment or proximal structural segment use elastic elongated tubes, the structural backbones of the next distal structural segment or proximal structural segment can pass through the elastic elongated tubes or directly pass through the structural backbone passage holes in the distal spacer disks or the proximal spacer disks. In this way, further miniaturization can be achieved without changing the relative motion relationship of the various structural segments in the distal structural body 11 or proximal structural body 12. As shown in FIGS. 3 and 4, for example, in the case where the distal structural body 11 comprises a first distal structural segment 112 and a second distal structural segment 113, the second distal structural segment 113 can remain stationary while the first distal structural segment 112 is moved. The relative arrangement of the proximal structural segments in the proximal structural body 12 may be series connection, nested arrangement (as shown in FIG. 5), independent arrangement, etc., which is not limited in the present application. However, it should be noted that the number of the distal structural segments in the distal structural body 11 should be consistent with the number of the proximal structural segments in the proximal structural body 12. It should be explained that "front" herein corresponds to "distal", and "rear" corresponds to "proximal".

Figure 6:
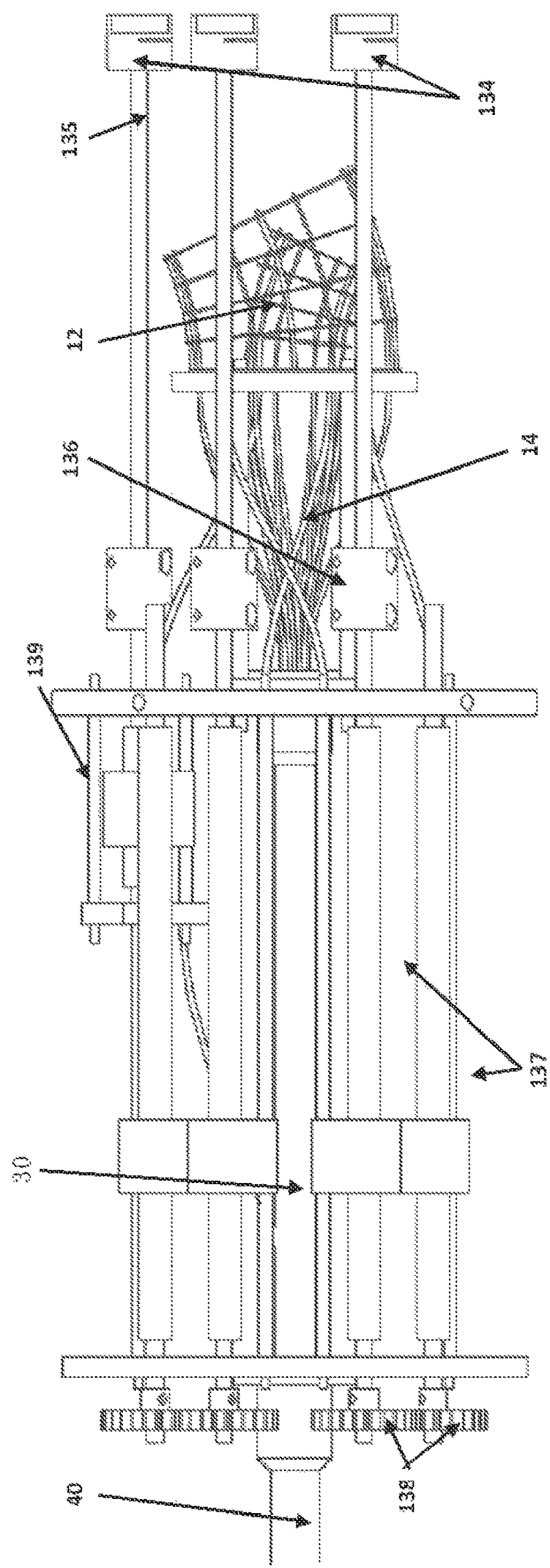
FIG. 6 is a structural schematic diagram of a driving transmission mechanism, a middle connecting body, and a proximal structural body shown in accordance with an example of the present application.
Figure 7:
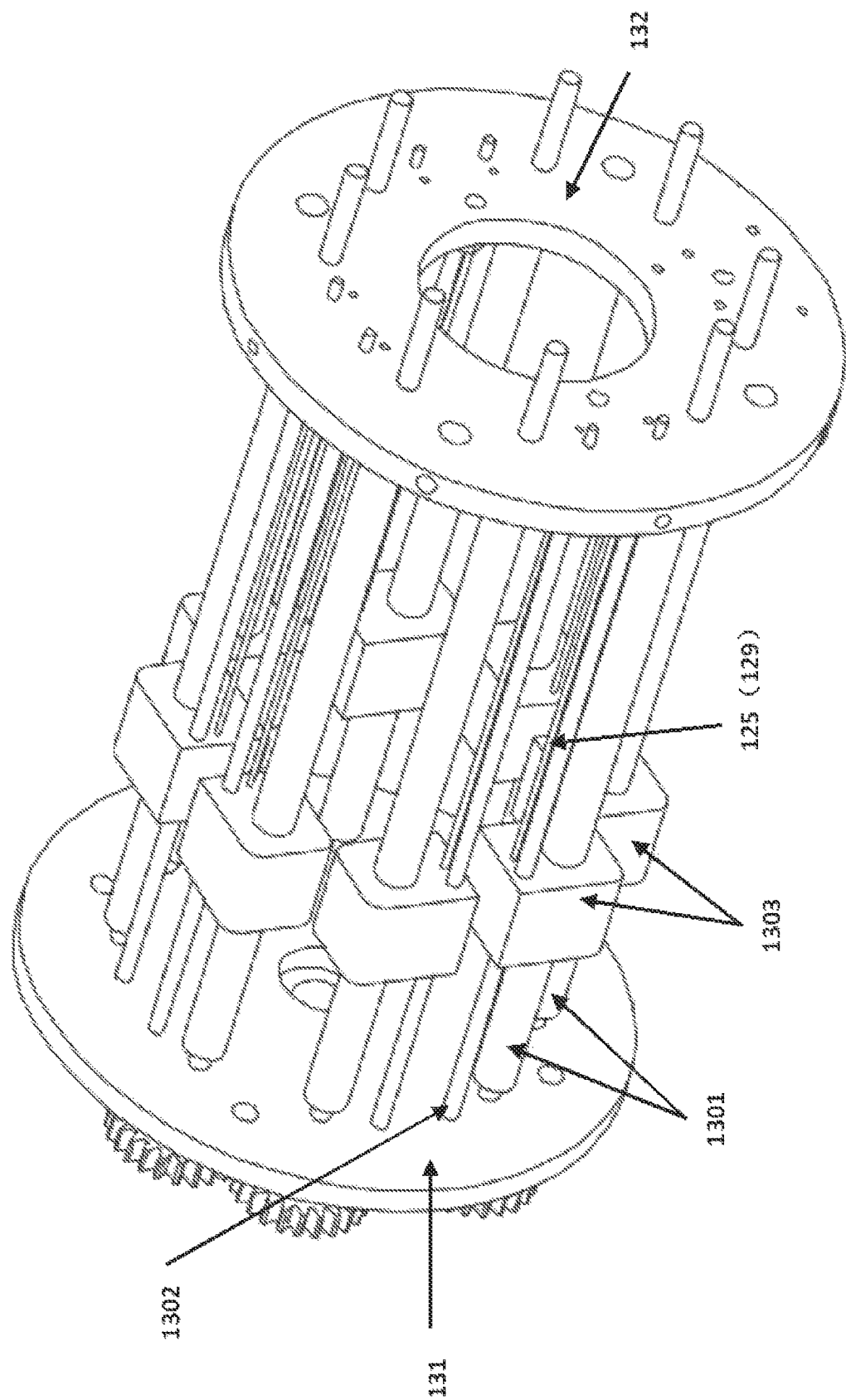
FIG. 7 is a structural schematic diagram of a driving transmission mechanism shown in accordance with an example of the present application, but viewed from another angle.

As shown in FIGS. 2, 6 and 7, the driving transmission mechanism 13 may comprise a main body part, an introducing part, a driving part, and a reversing part. As shown in FIG. 2, the main body part may comprise a distal cover plate 130, a distal fixing plate 131, a middle fixing plate 132, and a proximal fixing plate 133, which are securely connected to form an integral body via fixing plate connection columns 1300.

As shown in FIG. 6, the introducing part may comprise a first male coupling 134, a driving shaft 135, and a first coupling 136. The driving shaft 135 may be rotatably mounted between the proximal fixing plate 133 and the middle fixing plate 132, and the proximal end of the driving shaft passes through the proximal fixing plate 133 and is then fixedly connected to the first male coupling 134, and the distal end thereof is fixedly connected to the first coupling 136. The first male coupling 134 may be linked to the driving unit 20. The driving shaft 135 may be configured to drive the flexible surgical instrument. The driving part may comprise a plurality of sets of linear driving mechanisms 137. In this embodiment, four sets of, i.e., a total of eight linear driving mechanisms 137 are used, the two linear driving mechanisms 137 of the same set can simultaneously output a cooperative pushing/pulling motion, and the four sets of linear driving mechanisms 137 can achieve four degrees of freedom of turning of the first proximal structural segment 120 and the second proximal structural segment 121. The number of the linear driving mechanisms 137 should be equal to the sum of the numbers of the first segment driving backbones 125 and the second segment driving backbones 129. One set of linear driving mechanisms 137 may be connected to two driving backbones belonging to the same structural segment.

As shown in FIG. 7, each linear driving mechanism 137 may comprise a first threaded rod 1301 rotatably mounted between the distal fixing plate 131 and the middle fixing plate 132, a shaft 1302 securely arranged between the distal fixing plate 131 and the middle fixing plates 132, and a first slider 1303 slidably connected to the shaft 1302 and threadedly fitted with the first threaded rod 1301. Eight first sliders 1303 may be used as output ends of the linear driving mechanisms 137 and are securely connected to four first segment driving backbones 125 and four second segment driving backbones 129, respectively. The proximal end of the first threaded rod 1301 passes through the middle fixing plate 132 and is then securely connected to the first coupling 136, and the distal end thereof passes through the distal fixing plate 131 and then extends into the reversing part.

As shown in FIG. 6, the reversing part may comprise a plurality of sets of reversing gears 138 mounted between the distal cover plate 130 and the distal fixing plate 131, and the number of the sets of reversing gears 138 may be consistent with the number of the sets of the linear driving mechanisms 137. Each set of reversing gears 138 may comprise two intermeshing gears that are securely connected to two first threaded rods 1301, respectively. Two linear driving mechanisms 137 connected to one set of reversing gears may be one set of linear driving mechanisms as described above.

The rotational power from the driving unit 20 is transmitted to the first threaded rod 1301 located inside the driving part through the first male coupling 134, the driving shaft 135 and the first coupling 136, which are securely connected to one another, and passes through the reversing part, each set of reversing gears 138 drive the corresponding two first threaded rods 1301 to rotate in opposite directions, and the two first threaded rods 1301, which are provided with threads having the same spiral direction, can respectively drive the two first sliders 1303 to slide in opposite directions along the two shafts 1302, thereby converting the rotational power into a linear power for cooperatively pushing or pulling two first segment driving backbones 125 or second segment driving backbones 129. Two sets of linear driving mechanisms 137 can turn the first proximal structural segment 120 in any direction, and in turn drive the first distal structural segment 112 to turn in the opposite direction in a certain proportional relationship. The proportional relationship may be determined jointly by the distribution radii of the first segment structural backbones 116 and the first segment structural backbones 124. Similarly, the other two sets of linear driving mechanism 137 can turn the second proximal structural segment 121 in any direction, and in turn drive the second distal structural segment 113 to turn in the opposite direction in a certain proportional relationship. The proportional relationship may be determined jointly by the distribution radii of the second segment structural backbones 119 and the second segment structural backbones 128.

Figure 8:
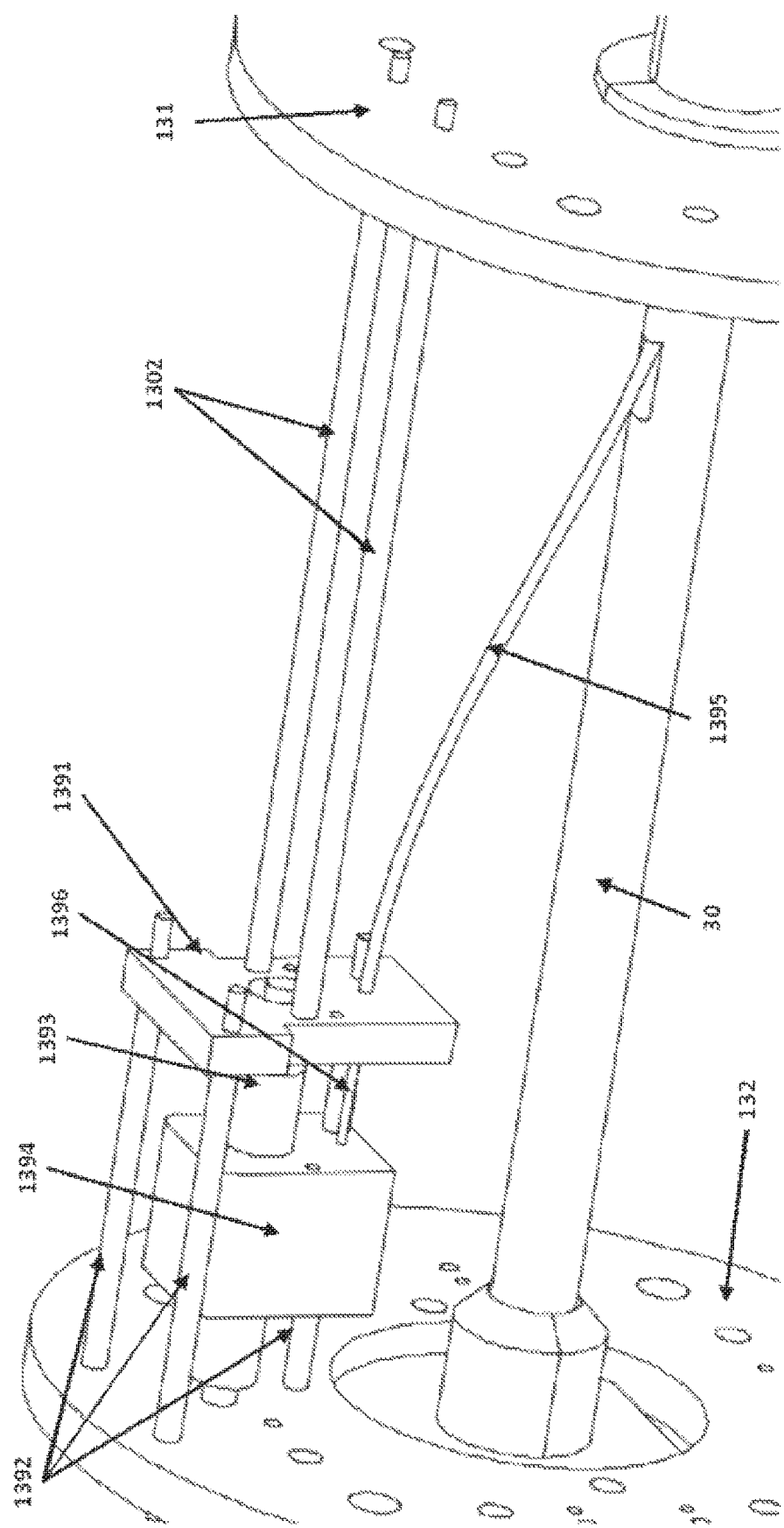
FIG. 8 is a structural schematic diagram of a surgical end effector driving mechanism shown in accordance with an example of the present application.

As shown in FIGS. 6 and 8, the driving transmission mechanism 13 further comprises a surgical end effector driving mechanism 139. The surgical end effector driving mechanism 139 may comprise a fixing end plate 1391, support columns 1392, a second threaded rod 1393, a second slider 1394, a actuation wire guide channel 1395, and a surgical end effector actuation wire 1396. The fixing end plate 1391 may be fixed onto the middle fixing plate 132 via several support columns 1392. The second threaded rod 1393 may be rotatably mounted between the fixing end plate 1391 and the middle fixing plate 132, and the proximal end of the second threaded rod 1393 passes through the middle fixing plate 132 and is then securely connected to the first coupling 136. The second slider 1394 is threadedly fitted with the second threaded rod 1393 and slidably connected to the support column 1392. The proximal end of the actuation wire guide channel 1395 is fixed onto the fixing end plate 1391, and the distal end thereof extends into the first distal structural segment 112 and is fixed onto the first distal spacer disk 114 (not shown in FIG. 8), for example, the distal end of the actuation wire guide channel 1395 may be fixed onto the first distal spacer disk closest to the proximal end thereof. The proximal end of the surgical end effector actuation wire 1396 is securely connected to the second slider 1394, and the distal end thereof passes through the fixing end plate 1391, the actuation wire guide channel 1395 and the distal structural body 11 and is then securely connected to the surgical end effector 111. The actuation wire guide channel 1395 may maintain its shape when the surgical end effector actuation wire 1396 is subjected to a pushing or pulling force.

Figure 9:
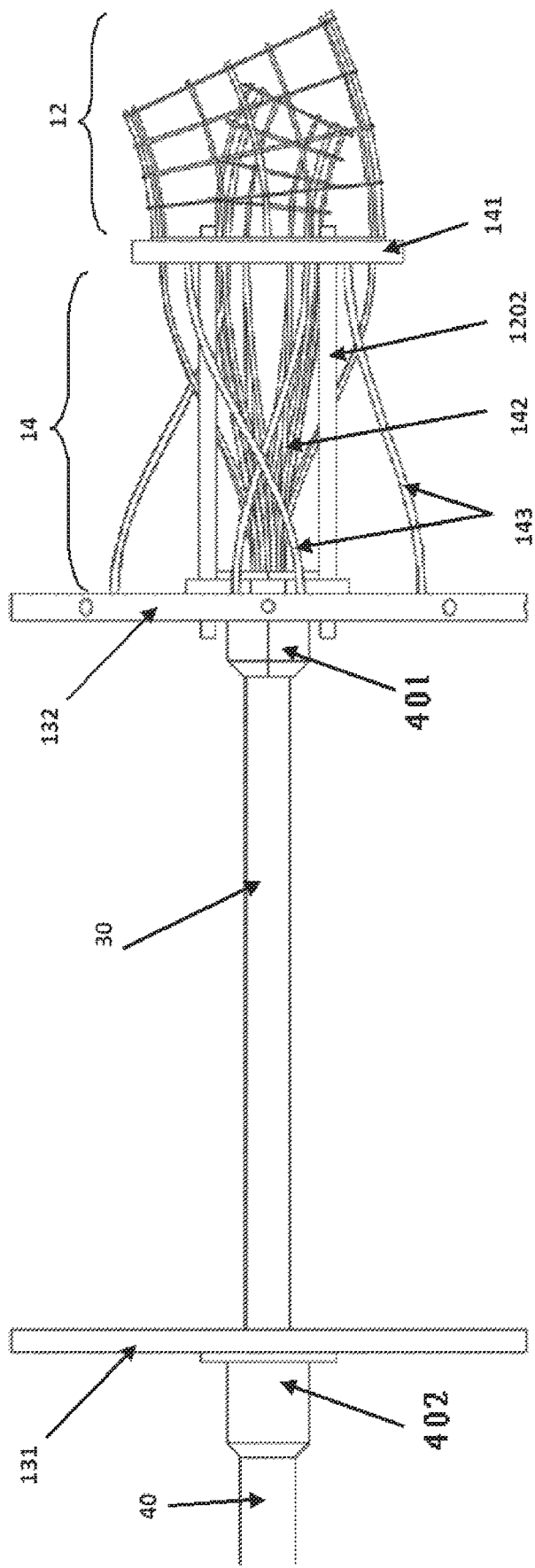
FIG. 9 is a structural schematic diagram of a middle connecting body and a proximal structural body shown in accordance with an example of the present application.

The rotational power generated by the driving unit 20 is transmitted to the second threaded rod 1393 through the first male coupling 134, the driving shaft 135 and the first coupling 136 which are securely connected to one another, and the second threaded rod 1393 may drive the second slider 1394 thereon to linearly slide along the support column 1392 and in turn push or pull the surgical end effector actuation wire 1396 to control the action of the mechanical surgical end effector 111 (such as surgical forceps). It will be understood by those skilled in the art that the surgical end effector actuation wire 1396 can also transmit energy, such as electric energy and ultrasonic vibration, to the surgical end effector 111 (such as an electric knife and an ultrasonic knife) so as to perform an electrosurgical operation As shown in FIG. 9, the middle connecting body 14 may comprise a proximal structural body fixing end disk 141, structural backbone guide channels 142, and driving backbone guide channels 143. The distal ends of the structural backbone guide channels 142 may be bundled and fixedly connected to the middle fixing plate 132, and the proximal ends thereof may be fixedly connected to the proximal structural body fixing end disk 141 for guiding the first segment structural backbones 116 (124) and the second segment structural backbones 119 (128) to maintain their shapes under a pushing or pulling force. Therefore, the number of the structural backbone guide channels 142 should be equal to the sum of the numbers of the first segment structural backbones 116 (124) and the second segment structural backbones 119 (128).

Two ends of the driving backbone guide channel 143 may be fixedly connected to the middle fixing plate 132 and the proximal structural body fixing end disk 141, respectively. The distal ends of the first segment driving backbone 125 and the second segment driving backbone 129 may be fixedly connected inside the linear driving mechanism 137, and the proximal ends thereof may be guided by the driving backbone guide channels 143 and then fixedly connected to the first proximal fixing disk 122 and the second proximal fixing disk 126 respectively, to maintain the shapes of the first segment driving backbone and the second segment driving backbone under a pushing or pulling force. Therefore, the number of the driving backbone guide channels 143 should be equal to the sum of the numbers of the first segment driving backbones 125 and the second segment driving backbones 129.

Figure 10:
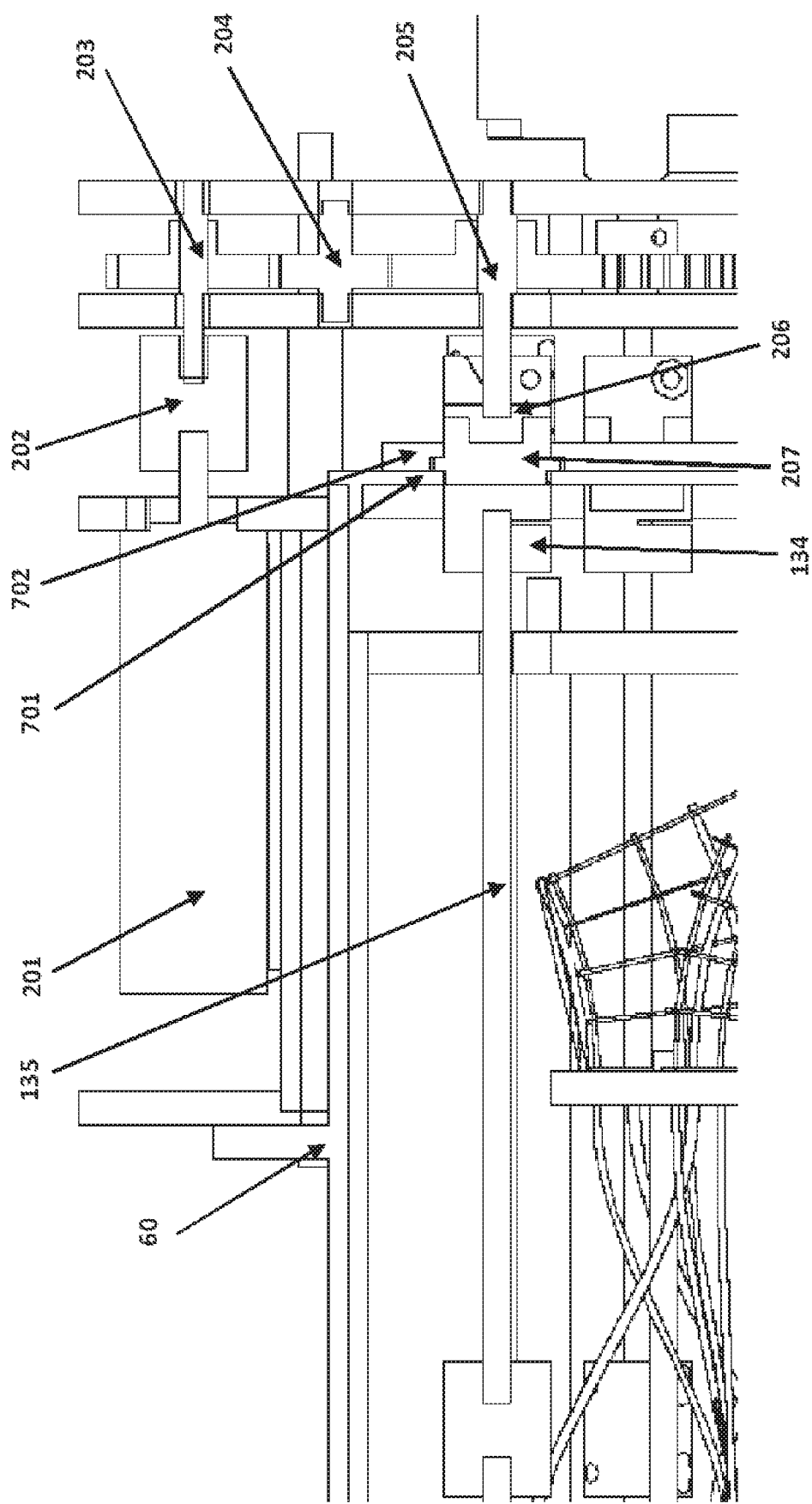
FIG. 10 is a structural schematic diagram of a driving unit shown in accordance with an example of the present application.
Figure 11:
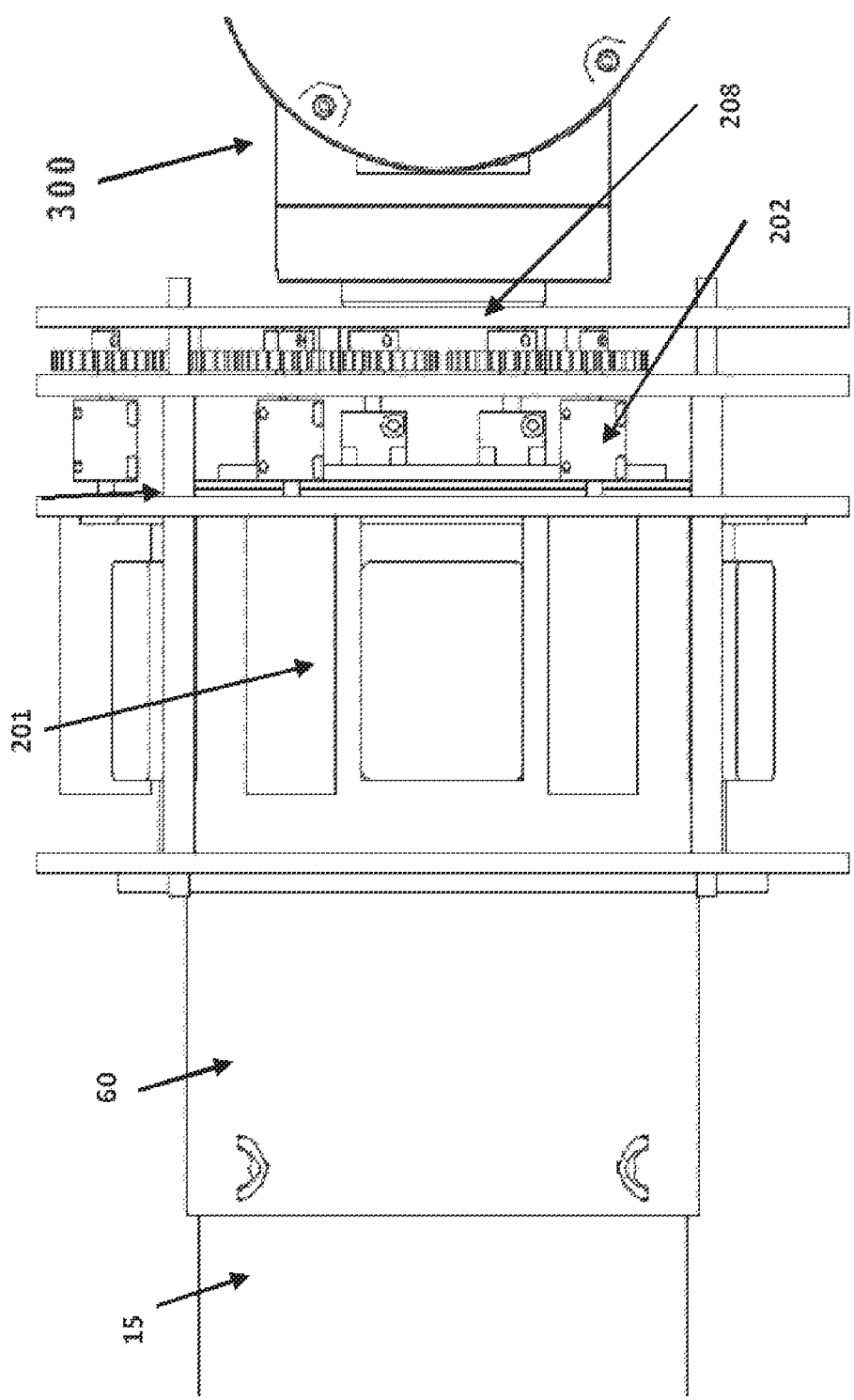
FIG. 11 is a schematic diagram showing the connection between a driving unit and a multi-degree-of-freedom robotic arm shown in accordance with an example of the present application.

As shown in FIGS. 10 and 11, the driving unit 20 may comprise a driving motor 201, a second coupling 202, an input gear 203, an idle gear 204, an output gear 205, a second male coupling 206, and female couplings 207. The second coupling 202 may be fixedly connected to an output shaft of the driving motor 201 and the input gear 203, respectively. The input gear 203, the idle gear 204 and the output gear 205 mesh with one another. The second male coupling 206 is fixedly connected to the output gear 205. The female couplings 207 may be connected to the second male coupling 206 and the first male coupling 134 in the driving transmission mechanism 13, respectively. In this way, the driving motor 201 can transmit the rotational motion to the second male coupling 206 through the second coupling 202, the input gear 203, the idle gear 204 and the output gear 205, and drive the driving shaft 135 to rotate by means of the female couplings 207 and the first male coupling 134 in the driving transmission mechanism 13. In an embodiment, the driving unit 20 may not comprise the second coupling 202. In this case, a through hole may be provided in the center of the input gear 203, and a motor shaft of the output motor 201 may directly extend into the through hole.

Figure 12:
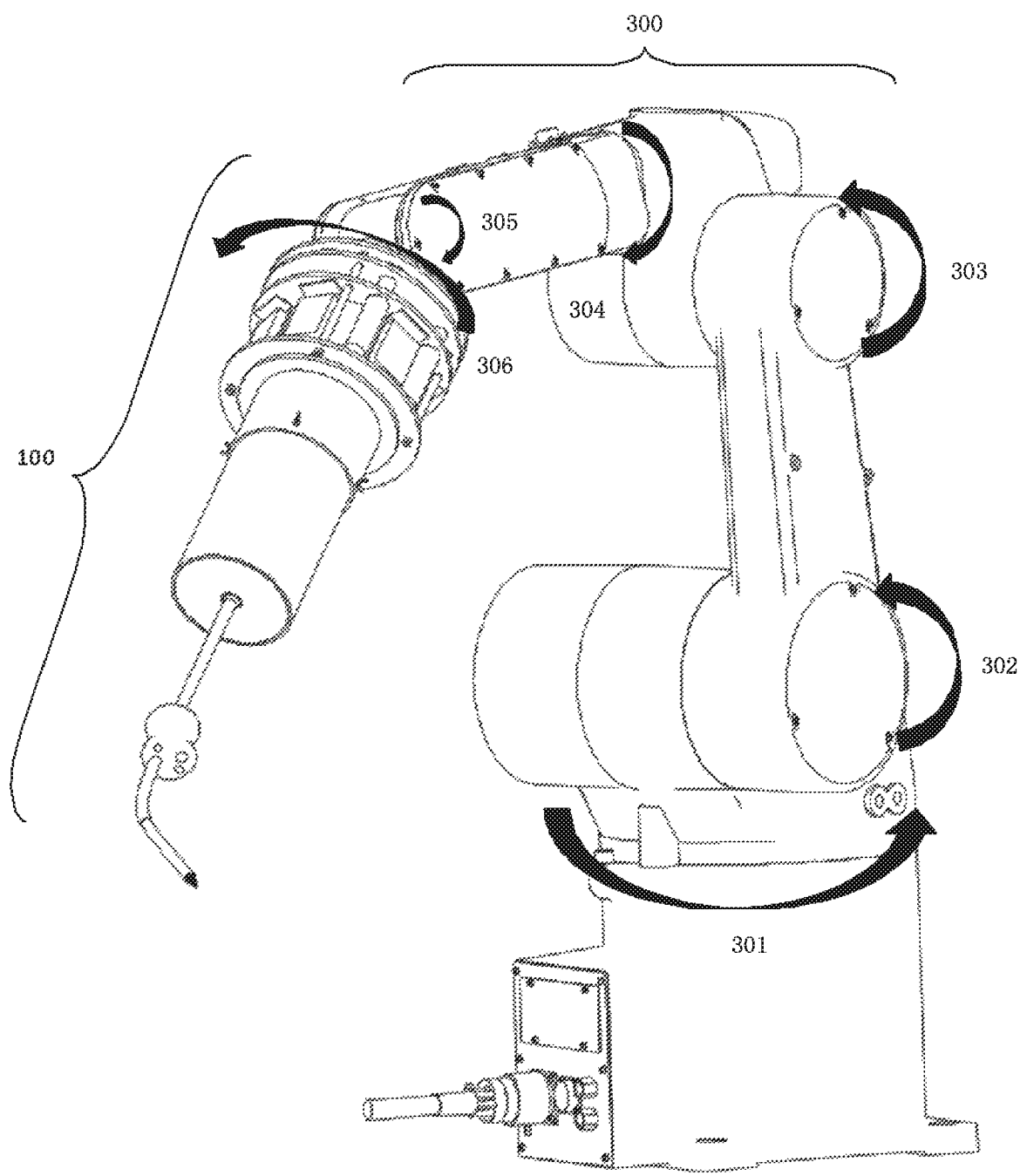
FIG. 12 is a schematic diagram of a flexible surgical instrument connected to a multi-degree-of-freedom robotic arm shown in accordance with an example of the present application.

FIG. 12 is a schematic diagram of a flexible surgical instrument system 100 connected to a multi-degree-of-freedom robotic arm 300 shown in accordance with an example of the present application. A connection plate 208 (as shown in FIG. 11) is provided at one end of the driving unit 20. The flexible surgical instrument system 100 may be mounted and fixed onto the multi-degree-of-freedom robotic arm 300 via the connection plate 208. The multi-degree-of-freedom robotic arm 300 may comprise six rotary joints 301-306, wherein the first five rotary joints 301-305 can implement the overall lateral rotation and the overall feed freedom of the flexible surgical instrument system 100 with an abdomen entrance point as the fixed point, and the rotary joint 306 can implement the overall rotation freedom of the flexible surgical instrument system 100 about its own axis. Consequently, the multi-degree-of-freedom robotic arm 300 enables a large-scale motion of the flexible surgical instrument system 100, and the flexible surgical instrument system 100 can realize a small-scale precise and flexible motion of the distal structural body 11 in the body of the patient and the driving of the surgical end effector 111.

Figure 13:
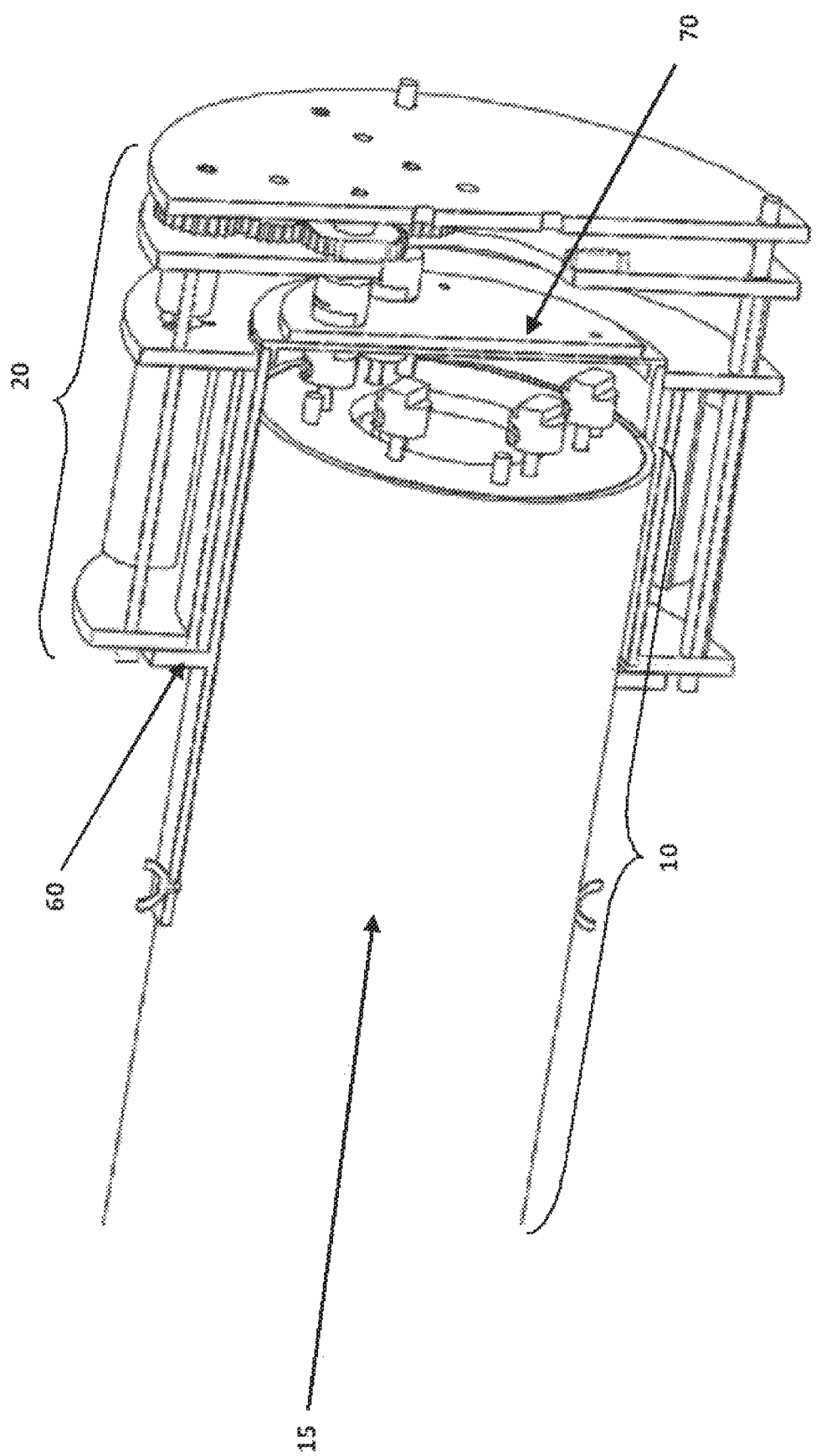
FIG. 13 is a structural schematic diagram of a flexible surgical instrument with a sterile barrier and a driving unit having been mounted thereto shown in accordance with an example of the present application.

In an embodiment, as shown in FIGS. 10, 11 and 13, the flexible surgical instrument 10 may further comprise a flexible surgical instrument housing 15. In this case, the distal cover plate 130 may form a housing structure of the flexible surgical instrument 10 with the flexible surgical instrument housing 15, and the proximal structural body 12, the driving transmission mechanism 13 and the middle connecting body 14 may be all located inside the flexible surgical instrument housing 15.

Since the flexible surgical instrument 10 is a sterilizable purely-mechanical structure, and the driving unit 20 is a non-sterilizable electrical structure, the present invention may be further provided with a sterile barrier 70, as shown in FIGS. 10 and 13, between the flexible surgical instrument 10 and the driving unit 20. The sterile barrier 70 may comprise a structural fixing cylinder 60, a sterile barrier cover plate 701, a sterile barrier base plate 702, and a sterile membrane (not shown). The structural fixing cylinder 60 may be connected to the flexible surgical instrument 10 and the driving unit 20, respectively. The sterile barrier cover plate 701 and the sterile barrier base plate 702 may be fixedly connected to the structural fixing cylinder 60 to form an integral body. Moreover, the structural fixing cylinder 60, the sterile barrier cover plate 701, and the plurality of female couplings 207 may form a closed structure inside the driving unit 20 for isolating a bacterial environment from the sterile environment. The female couplings 207 in the driving unit 20 may be rotatably arranged between the sterile barrier cover plate 701 and the sterile barrier base plate 702. Therefore, the free rotation of the female coupling 207 at a fixed axis position can be achieved by rational selection of materials of the sterile barrier cover plate 701 and the sterile barrier base plate 702, such as Teflon. The unsterilized driving unit 20 and the multi-degree-of-freedom robotic arm 300 may be externally covered with the sterile membrane at an outer edge of the structural fixing cylinder 60, for separating the sterilized and unsterilized parts to ensure the clinical practicability of surgery.

In an embodiment, as shown in FIGS. 2, 6 and 9, the distal structural body 11 is externally coated with an envelope 30. The proximal end of the envelope 30 may be securely connected to the middle fixing plate 132 via a first fixing clamp 401. The envelope 30 may be a rigid envelope between the distal fixing plate 131 and the middle fixing plate 132 to ensure the structural stability of the distal structural body 11. The envelope 30 may be a flexible envelope between the distal fixing plate 131 and the surgical end effector 111 to improve the appearance and insertion smoothness of the distal structural body 11.

In an embodiment, as shown in FIGS. 2, 6 and 9, the envelope 30 may be externally coated with an outer sleeve 40. The outer sleeve 40 may be fixed onto the distal fixing plate 131 via a second fixing clamp 402. In different surgical environments, the outer sleeve 40 can be replaced and adjusted by simply releasing the second fixing clamp 402.

The outer sleeve 40 may be a rigid pre-bent sleeve. At this point, the outer sleeve 40 may pass through a sheath 50 (as shown in FIGS. 2 and 3) fixed to a single incision in the abdominal cavity. The sheath 50 may provide a channel for instruments (typically three surgical instruments and one imaging illumination instrument) required for the single-port laparoscopic surgery, wherein the channel may be an oblique channel and does not limit the lateral rotation motion of the surgical instrument about a particular fixed point (e.g., the intersection point between an axis of the channel in the sheath 50 and the skin incision). The rigid pre-bent outer sleeve 40 and the distal structural body 11, together with the envelope 30 and the surgical end effector 111, can freely pass through a through hole in the sheath 50 for the passage of the surgical instrument and have access to the surgical site to perform the single-port laparoscopic surgery.

Alternatively, the outer sleeve 40 may also be a rigid straight sleeve. At this point, the outer sleeve 40 may pass through a sheath 50 (as shown in FIG. 4) containing only one channel. The sheath 50 may be fixed to the skin incision in the abdominal cavity. Multiple flexible surgical instrument systems 100 with multiple sheaths 50 can be used for performing the multi-port laparoscopic surgery. It should be explained that the flexible surgical instrument system 100 can adjust with the multi-degree-of-freedom robotic arm 300 the direction of the outer sleeve 40 and the distal structural body 11 therein and the distance by which same extend out of the sheath 50, further improving the motion performance of the distal structural body 11.

The present invention has been illustrated only by the above embodiments, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument, comprising:
a distal structural body comprising at least one distal structural segment each comprising a distal fixing disk and structural backbones;
a proximal structural body comprising at least one proximal structural segment each comprising a proximal fixing disk, structural backbones, and driving backbones, the structural backbones of the distal structural segment being securely connected in one-to-one correspondence to or the same as corresponding structural backbones of the proximal structural segment; and
a driving transmission mechanism to push or pull the driving backbones to turn the proximal structural segment;
wherein first ends of the driving backbones are fixed onto the proximal fixing disk, and second ends of the driving backbones are fixed in the driving transmission mechanism.

2. The flexible surgical instrument of claim 1, wherein proximal ends of the structural backbones of the proximal structural segment are securely connected to the proximal fixing disk, and distal ends of the structural backbones of the distal structural segment are securely connected to the distal fixing disk.

3. The flexible surgical instrument of claim 1, wherein the driving transmission mechanism comprises a driving part to convert the rotational power into a linear power to cooperatively push or pull the driving backbones to turn the proximal structural segment.

4. The flexible surgical instrument of claim 3, wherein the driving part comprises a plurality of sets of linear driving mechanisms, each set of linear driving mechanisms being to output a cooperative push/pull motion, the linear driving mechanism comprises a first threaded rod, and a first slider threadedly fitted with the first threaded rod;
the first sliders of each set of the linear driving mechanisms are securely connected to corresponding driving backbones.

5. The flexible surgical instrument of claim 3, wherein the driving transmission mechanism further comprises:
an introducing part to introduce an outside rotational power into the driving part;
a reversing part to implement a cooperative motion of the driving part;
the outside rotational power is transmitted to the driving part through the introducing part and the reversing part.

6. The flexible surgical instrument of claim 4, wherein the driving transmission mechanism further comprises:
an introducing part to introduce an outside rotational power into the driving part, the introducing part comprising a driving shaft;
a reversing part comprising several sets of reversing gears, each set of reversing gears comprising two intermeshing gears securely connected to two first threaded rods of each set of two linear driving mechanisms, respectively;
the outside rotational power is transmitted to one of the two first threaded rods through the driving shaft, and drives the two first threaded rods to rotate in opposite directions with the set of reversing gears.

7. The flexible surgical instrument of claim 6, wherein the driving transmission mechanism further comprises a main body part comprising a distal cover plate, a distal fixing plate, a middle fixing plate, and a proximal fixing plate;
the driving shaft is rotatably mounted between the proximal fixing plate and the middle fixing plate;
the first threaded rod is rotatably mounted between the distal fixing plate and the middle fixing plate; and
the set of reversing gears are mounted between the distal cover plate and the distal fixing plate.

8. The flexible surgical instrument of claim 7, wherein the linear driving mechanism further comprises a shaft fixedly connected between the distal fixing plate and the middle fixing plate, and
the first slider is slidably connected to the shaft.

9. The flexible surgical instrument of claim 1, further comprising: a middle connecting body comprising a proximal structural body fixing end disk and structural backbone guide channels, wherein
distal ends of the structural backbone guide channels are fixedly connected to the driving transmission mechanism, and proximal ends of the structural backbone guide channels are fixedly connected to the proximal structural body fixing end disk, and
the structural backbones of the distal structural segment pass through the structural backbone guide channels and the distal ends of the structural backbones of the distal structural segment are securely connected to the distal fixing disk.

10. The flexible surgical instrument of claim 1, further comprising a surgical end effector located at a distal end of the distal structural body, and
the driving transmission mechanism further comprises a surgical end effector driving mechanism.

11. The flexible surgical instrument of claim 10, wherein the surgical end effector driving mechanism comprises:
a second threaded rod;
a second slider threadedly fitted with the second threaded rod; and
a surgical end effector actuation wire passing through the distal structural body and comprising a proximal end securely connected to the second slider and a distal end securely connected to the surgical end effector.

12. The flexible surgical instrument of claim 11, wherein the driving transmission mechanism further comprises a main body part that comprises a middle fixing plate, and
the surgical end effector driving mechanism further comprises:
a fixing end plate fixed onto the middle fixing plate, and
an actuation wire guide channel with a proximal end fixed onto the fixing end plate and a distal end extending into the distal structural segment and fixed onto a distal spacer disk of the distal structural segment,
the second threaded rod is rotatably mounted between the fixing end plate and the middle fixing plate,
the surgical end effector actuation wire passes through the fixing end plate, the actuation wire guide channel and the distal structural body;
a proximal end of the surgical end effector actuation wire is securely connected to the second slider, and
a distal end of the surgical end effector actuation wire is securely connected to the surgical end effector.

13. The flexible surgical instrument of claim 1, wherein the distal structural segment further comprises a plurality of distal spacer disks distributed at intervals, the structural backbones of the distal structural segment pass through structural backbone passage holes distributed in each of the distal spacer disks, and the distal ends of the structural backbones of the distal structural segment are fixed onto the distal fixing disk; and
the proximal structural segment further comprises a plurality of proximal spacer disks distributed at intervals,
the structural backbones of the proximal structural segment pass through structural backbone passage holes distributed in the proximal spacer disks in sequence, and
the proximal ends of the structural backbones of the proximal structural segment are fixed on the proximal fixing disk and the distal ends of the structural backbones of the proximal structural segment are securely connected in one-to-one correspondence to or are the same as the structural backbones of the distal structural segment.

14. The flexible surgical instrument of claim 13, wherein a distal structural body comprises a plurality of the distal structural segments or a proximal structural body comprises a plurality of the proximal structural segments,
the structural backbones of a preceding distal structural segment or proximal structural segment use elastic elongated tubes, the structural backbones of a next distal structural segment or proximal structural segment are able to pass through the elastic elongated tubes or directly pass through the structural backbone passage holes in the distal spacer disks or in the proximal spacer disks, respectively.

15. The flexible surgical instrument of claim 1, wherein the flexible surgical instrument further comprises a middle connecting body comprising:
a proximal structural body fixing end disk,
structural backbone guide channels, comprising distal ends fixedly connected to the driving transmission mechanism, and proximal ends fixedly connected to the proximal structural body fixing end disk; and
driving backbone guide channels comprising distal and proximal ends fixedly connected to the driving transmission mechanism and the proximal structural body fixing end disk, respectively,
proximal ends of the structural backbones of the proximal structural segment are securely connected to the proximal fixing disk, distal ends of the structural backbones of the distal structural segment are securely connected to the distal fixing disk, and
the structural backbones of the proximal structural segment and the structural backbones of the distal structural segment pass through the structural backbone guide channels.

16. A flexible surgical instrument system, comprising:
the flexible surgical instrument of claim 1, and
a driving unit to drive the driving transmission mechanism.

17. The flexible surgical instrument system of claim 16, further comprising:
a sterile barrier arranged between the flexible surgical instrument and the driving unit.

18. The flexible surgical instrument system of claim 17, wherein
the sterile barrier comprises:
a structural fixing cylinder connected to the flexible surgical instrument and the driving unit;

a sterile barrier cover plate;

a sterile barrier base plate fixedly connected to a proximal end of the structural fixing cylinder to form a closed structure; and a sterile membrane fixedly connected to an outer edge of the structural fixing cylinder and coated outside the driving unit.

19. The flexible surgical instrument system of claim 16, further comprising:

a robotic arm fixedly connected with a proximal end of the driving unit and to implement the overall lateral rotation and the overall feed freedom of the flexible surgical instrument system with an abdomen entrance point as fixed point.

* * * * *